(12) United States Patent
Lemaitre et al.

(10) Patent No.: US 6,425,949 B1
(45) Date of Patent: Jul. 30, 2002

(54) HYDRAULIC SURGICAL CEMENT

(75) Inventors: Jacques Lemaitre, Lausanne; Marc Bohner, Aarau; Pascale Van Landuyt, Ecublens, all of (CH)

(73) Assignees: Dr. H. C. Robert Mathys Stiftung, Bettlach; Stratec Medical AG, Oberdorf, both of (CH)

(*) Notice: Subject to any disclaimer, the term of this patent is extended or adjusted under 35 U.S.C. 154(b) by 0 days.

(21) Appl. No.: 09/529,054

(22) PCT Filed: Oct. 6, 1998

(86) PCT No.: PCT/EP98/06330

§ 371 (c)(1),
(2), (4) Date: Jul. 7, 2000

(87) PCT Pub. No.: WO99/17710

PCT Pub. Date: Apr. 15, 1999

(51) Int. Cl.$^7$ .......................... A61K 6/033; A61L 25/00; A61L 27/00
(52) U.S. Cl. ...................... 106/35; 106/691; 623/23.62; 501/1
(58) Field of Search .................. 106/35, 691; 501/1; 623/23.62

(56) References Cited

U.S. PATENT DOCUMENTS 5,152,836 A  10/1992  Hirano et al. ............... 106/690

FOREIGN PATENT DOCUMENTS

| | | | |
|---|---|---|---|
| DE | 42 16 496 A1 | 11/1993 | |
| EP | 543 765 A1 | 5/1993 | |
| GB | 2 260 977 A | 5/1993 | |

OTHER PUBLICATIONS

Mirtchi et al, "Calcium Phosphate Cements: Action of Setting Regulators on the Properties of the β–TricalciumP-phosphate–Monocalcium Phosphate cements", Biomaterials, vol. 10, pp. 634–638, Nov. 1989.*

* cited by examiner

Primary Examiner—C. Melissa Koslow
(74) Attorney, Agent, or Firm—Rankin, Hill, Porter & Clark LLP

(57) ABSTRACT

The cement for surgical purposes includes three components. The first component includes beta tertiary calcium-phosphate β-Ca$_3$(PO$_4$)$_2$(β-TCP) particles; and monocalcium phosphate Ca(H$_2$PO$_4$)$_2$(MCPA) or monocalcium phosphate monohydrate Ca(H$_2$PO$_4$).H$_2$O (MCPM) particles or phosphoric acid. The second component includes water. The third component includes particles having an average diameter which is larger than the average diameter of the beta tertiary calciumphosphate β-Ca$_3$(PO$_4$)$_2$(β-TCP) particles of the first component. Upon mixing of the three components a hardened mass comprising brushite CaHPO$_4$.2H$_2$O (DCPD) is formed. The β-TCP particles have a specific surface area of less than 10,000 m$^2$/g and a Ca/P atomic ratio different from 1.50. The component constitutes 1 to 99 volume-percent of the hardened mass. The cements according to the invention may be used in dental and maxillofacial surgery (alveolar ridge reconstruction, dental socket filling), for orthopaedic applications (bone fracture repair, bone augmentation) and for local drug delivery (antibiotics, anti-inflammatory and anti-cancer drugs).

34 Claims, No Drawings

HYDRAULIC SURGICAL CEMENT

BACKGROUND OF THE INVENTION

This invention concerns a cement for surgical purposes, a method for producing brushite as temporary bone replacement material, and a temporary bone replacement material.

A number of such hydraulic cements based on calcium phosphates for use in surgery are known in the prior art; they are prepared from two components (powder/liquid) by mixing them intra-operatively and applying them in pasteous consistency to the appropriate site where they harden in situ. The disadvantages of the prior art hydraulic cements based calcium phosphates are:

a. impracticable short setting times which do not allow their use for elaborate surgical procedures;

b. poor injectability, i.e. the fresh cement paste tends to clog the injection needle, and/or disintegrates in contact with physiological liquids, which prevents its implantation by minimal invasive surgery procedures;

c. low compacity, i.e. current hydraulic cements need larger amounts of mixing water in order to have them injectable or to confer them a convenient setting time, which results in very low ultimate mechanical strength after hardening.

In U.S. Pat. No. 4,880,610, a method is disclosed for making an in situ calcium phosphate mineral composition by combining water-free phosphoric acid crystals with a calcium source, which leads to a hydroxyapatite. It is clear that the use of 100% phosphoric acid in the operating room and the application of a paste containing 100% phosphoric acid in the human body must be considered a not ideal procedure that requires improvement. Furthermore the hydroxyapatite material produced by this known method will have a long resorption period, which is not commensurate to the rate of the bone remodelling. The disadvantage of prolonged resorption is that the bone treated by cement will remain for a prolonged time in abnormal biomechanical situation, which may develop secondary post-operational problems. Furthermore the unresorbed cement may still break down in pieces or fragments after prolonged mechanical loading, which increases the probability of post-operational complications, e.g. aseptic inflammatory reactions. The resorption rate of the ideal cement should match as closely as possible the spontaneous rate of new bone formation, which is around 20 micrometers per day.

From GB-2 260 977 a calcium phosphate composition is known using alpha-TCP particles. Alpha-TCP particles are much more reactive than beta-TCP particles and therefore lead to a setting time, when admixed to monocalcium phosphate monohydrate and water, that is much too fast (a few seconds), and hence difficult to control.

From an article of MIRCHI A A ET AL. appeared in Biomaterial 1989, Vol. 10, No. 9, Nov. 1, 1989, pages 634–638, a calcium phosphate cement is known with commercially available MCPM and β-TCP particles the Ca/P ratio of which is 1.50. The disadvantages of β-TCP particles with a Ca/P ratio of 1.50 is their relatively high reactivity which makes them inappropriate for a surgical cement.

SUMMARY OF THE INVENTION

The present invention is directed toward solving the above-described problems. The present invention provides a cement for surgical purposes, a method for producing a temporary bone replacement material, and a temporary bone replacement material.

DETAILED DESCRIPTION OF THE PREFERRED EMBODIMENT

The various features of novelty which characterize the invention are pointed out with particularity in the claims annexed to and forming part of this disclosure. For the better understanding of the invention, its operating advantages and specific objects attained by its use, reference should be done to the accompanying examples in which preferred embodiments of the invention are illustrated in detail.

The first component of the cement according to the invention comprises beta tertiary calciumphosphate β-$Ca_3(PO_4)_2$(β-TCP) particles in an amount preferably greater than about 50% by weight and one of the following substances:

monocalcium phosphate $Ca(H_2PO_4)_2$(MCPA) particles; or monocalcium phosphate monohydrate $Ca(H_{2PO4})_2 \cdot H_2O$ (MCPM) particles; or phosphoric acid.

Alternative a) and b) are the preferred ones; the phosphoric acid may be used either in solid or in liquid form.

The Ca/P atomic ratio of the β-TCP particles of the first component is preferably comprised between 1.35 to 1.499. Purposefully it is comprised between 1.45 to 1.47 and typically between 1.455 to 1.465. The advantage of the Ca/P atomic ratio used in the invention is the lower reactivity of the β-TCP particles. A lower Ca/P atomic ratio—below 1.5—can be achieved in avarious ways. One possiblity is the calcination and sintering of DCP [$CaHPO_4$]/hydroxyapatite [$Ca_5(PO_4)_3OH$]) mixtures. The Ca/P ratio is then controlled by the proportion of the two components. To obtain a Ca/P ratio of exactly 1.50 one should mix 10 g of DCP with 36.91 g HA. To obtain a Ca/P ratio of 1.35 one has to mix 10 g DCP with 13.6 g of HA. Alternatively DCP could be replaced by DCPD ($CaHPO_4 \cdot H_2O$), MCPM [$Ca(H_2PO_4)_2 \cdot H_2O$], CaPP ($Ca_2P_2O_7$) or OCP. The beta-TCP particles with a Ca/P ration inferior to 1.50 can also be obtained by adding small amounts of DCP, DCPD, MCPM or OCP to a pure beta-TCP powder, and then mix and sinter the mixture to homogenize it.

Another way is to add minor amounts of $Na_4P_2O_7 \cdot 10H_2O$ (NaPPH) to the β-TCP particles which retard their dissolution in a synergetic way. Consequently the setting time of the hydraulic cement is significantly increased. The presence of minor amounts of CaPPH increases also the sintering ability of the β-TCP particles, hence enabling the production of dense β-TCP particles. Non-dense β-TCP particles absorb the mixing liquid during setting. As a following, more mixing liquid must be used to knead the cement, provoking a decrease of the mechanical properties of the cement after hardening. If the amount of CaPPH is too large (Ca/P ratio below 1.35) the mechanical properties of the cement decrease drastically.

The mean specific surface area of the β-TCP particles must be less than 10 $m^2/g$ otherwise the cement has poor mechanical properties—due to a large porosity resulting from the large volume of mixing liquid—and a setting time which is too short for practical purposes. Preferably, the β-TCP particles have a mean specific surface area of 0.0137 to 2.000 $m^2/g$. More preferably, the β-TCP particles have a mean specific surface area of 0.8 to 1.5 $m^2/g$.

Setting time of the cement according to the invention as measured at 25° C. should be at least 2 minutes, typically at least 3 minutes and preferably at least 5 minutes.

According to a preferred embodiment of the invention the first component is divided into two subcomponents A and B, subcomponent A comprising the MCPA and/or MCPM particles and subcomponent B comprising the β-TCP particles and the setting rate controller.

The second component comprises water and may further comprise orthophosphoric acid (OPA) and/or sulphuric acid (SA), which again take the function of a setting rate controller and also lead to an improved microstructure of the final brushite (DCPD) crystals.

The third component comprises a calcium phosphate with a Ca/P ratio different from 1.5. The Ca/P ratio is preferably less than 1.5, more than 1.5, or more preferably in the range of 1.35 to 1.49. The third component comprises from 1–99 volume % of the hardened mass. The third component comprises particles having an average diameter which is larger than the average diameter of said beta tertiary calciumphophate β-Ca$_3$(PO$_4$)$_2$(β-TCP) particles of said first component.

After mixing the three components a hardened mass is formed comprising brushite CaHPO$_4$.2H$_2$O (DCPD), which based on its solubility is used to accelerate the resorption rate compared to HA.

The total weight $W_{TCP}$ of the β-TCP particles of the first and third components should preferably be larger than the stoichiometric weight $WT = W_{MCPA}/0.7546 + W_{MCPM}/0.8127 + W_{OPA}/03159 + W_{SA}/0.3162$ where $W_{MCPA}$, $W_{MCPM}$, $W_{OPA}$ and $W_{SA}$ are, respectively, the weights of MCPA, MCPM, OPA and SA used.

Further the weight $W_{TCP}$ should be in the range of 1.2 $W_T \leq W_{TCP} \leq 10.0$ $W_T$, and more preferably in the range of 2 $W_T \leq W_{TCP} \leq 5$ $W_T$.

The first component may further comprise a setting rate controller chosen from the group of sodium pyrophosphate, potassium pyrophosphate, sodium acetate, potassium acetate, sodium citrate, potassium citrate, sodium phosphocitrate, potassium phosphocitrate, sodium sulphate or potassium sulphate, calcium sulphate hemihydrate CaSO$_4$.0.5H$_2$O (CSH), sodium pyrophosphate Na4P$_2$O$_7$.10H$_2$O (NaPPH), sodium dihydrogen pyrophosphate Na$_2$H$_2$P$_2$O$_7$(NaHPP), calcium pyrophosphate Ca$_4$P$_2$O$_7$(CaPP), magnesium sulphate and sodium or potassium biphosphonate.

In a further preferred embodiment of the invention a third component consisting of particles having an average diameter which is larger than the average diameter of said beta tertiary calciumphosphate β-Ca$_3$(PO$_4$)$_2$(β-TCP) particles of said first component is added. This leads to conglomerate structure of the finally set cement, whereby the third component particles are embedded in the brushite matrix formed by the setting process. The average particle diameter of said third component should be at least two times larger, preferably at least 10 times larger compared to the average diameter of the beta tertiary calciumphosphate β-Ca$_3$(PO$_4$)$_2$(β-TCP) particles of the first component. Preferably the average particle diameter of said third component should be in the range of 50 to 2000 μm. The particles of the third component may consist of hydroxyapatite particles or of polymeric particles, e.g. lactides, polysaccharides, collagenes or proteins.

In a further preferred embodiment of the invention two different types of β-TCP particles are used, the first type being particles having a median particle size of 5 μm with less than 10 volume % of the particles being smaller than 1 μm; and the second type being particles having an average diameter in the range of 150 to 500 μm, preferably in the range of 250 to 400 μm. The average particle diameter of said third component should be in the range of 50 to 2000 μm, preferably between 250 and 750 μm.

The volume $V_L$ of the second component should preferably be equal or superior than the volume $V_T = (W_{MCPA} \times 0.615 + W_{MCPM} \times 0.5 + W_{OPA} \times 1.102 + W_{SA} 1.101)$ ml/g of the first component. The volume $V_L$ is typically in the range of 0.5 $V_T \leq V_L \leq 10.0$ $V_T$, preferably in the range of 1.2$V_T \leq V_L \leq 2.0$ $V_T$.

One of the two components may further comprise a biodegradable polymer for controlling the consistency of the cement paste resulting from mixing of the two components, and its cohesion in physiological liquids. The biodegradable polymer may be selected from the group of polysaccharide derivatives, preferably hyaluronic acid, dextran, hydroxypropyl-methyl cellulose; chitin derivatives, preferably chitosan; xanthan gum; agarose; polyethyleneglycols (PEG), polyhydroxyethylenemethacrylats (HEMA), synthetic and natural proteins or collagens.

The first component may further comprise pharmaceutically or physiologically active substances, preferably selected from the group of antibiotics, anti-inflammatory, anti-cancer drugs and bone growth factors. The antibiotics is preferably a gentamycin or a gentamycin salt, typically gentamycin sulphate. Other gentamycin salts can be used provided their solubility is in the range of 100 to 2500 mg/l. The antibiotics is selected from the group of aminoglycosides, vancomycins, gentamycins or salts thereof, preferably gentamycin sulphate or gentamycin crobefat. The antibiotics can comprise a mixture of aminoglycosides, such as a mixture of vancomycin with gentamycin, which is preferred.

The cements according to the invention may be used as bone substitute in dental and maxillofacial surgery (alveolar ridge reconstruction, dental socket filling), for orthopaedic applications (bone fracture repair, bone augmentation) and for local drug delivery (antibiotics, anti-inflammatory and anti-cancer drugs).

In a preferred embodiment the particles of the third component are made from another material than beta tertiary calciumphosphate β-Ca$_3$(PO$_4$)$_2$(β-TCP). The particles of said third component are preferably made from a material selected from the group of: hydroxyapatite; biphasic calcium phosphonate (BCP) (HA/β-TCP) mixtures; bioglasses; or polymeric materials. The advantage is the differential degradation of such a cement. The matrix of the cement is degraded faster than the residual granulates. This is particularly useful for the application in the osteoporose field or for the ridge reconstruction of the jaw, where a slower degrading granulate, e.g. made from hydroxyapatite or BCP is desired.

Five specific examples are reported below for producing the temporary bone replacement materials according to the invention.

EXAMPLE 1

The first component (containing the powdered particles) consists of two separate subcomponents A and B.

Subcomponent A consist of:
a. 0.80 g of monocalcium phosphate monohydrate Ca(H$_2$PO$_4$)$_2$.H$_2$O MCPM particles.

Subcomponent B is a mixture of:
a. 1.20 g of beta tertiary calciumphosphate β-Ca$_3$(PO$_4$)$_2$ (β-TCP) particles having a Ca/P atomic ratio in the range of 1.44 to 1.47. The median particle size of the β-TCP particles is 5 μm and its specific surface area is less than 2 m$^2$/g; and
b. 0.012 g sodium pyrophosphate Na$_2$H$_2$P$_2$O$_7$.

The second component (containing the liquid) consists of 0.80 to 0.90 ml of a 0.10 M aqueous sulphuric acid solution.

The third component comprises particles having an average diameter that is larger than the average diameter of the beta tertiary calciumphosphate β-Ca$_3$(PO$_4$)$_2$(β-TCP) particles of the first component. The third component, which may be admixed to the first component as Subcomponent C, contains 0.5 g (β-TCP) particles with a diameter comprised in the range of 0.5 to 0.71 mm and a Ca/P atomic ratio in the range of 1.46.

The powdered subcomponents are sterilized by gamma-irradiation. The liquid component is prepared in sterile conditions with sterile materials.

The hydraulic cement paste is prepared by using a pestle. Subcomponent A is carefully mixed with the liquid component in a mortar for approximately 1 minute. Thereafter subcomponent B is added and kneaded carefully with a spatula for about a minute, until a uniform paste is obtained. The paste can be used for about 10 minutes, depending on ambient temperature; the higher the temperature, the shorter the setting time. Using refrigerated material and preparation instruments helps in prolonging the available working time.

EXAMPLE 2

The first component (containing the powdered particles) consists of 1.3 g of β-TCP particles with an average diameter of 6 μm and a Ca/P molar ratio of 1.41 and 0.7 g of MCPM. The third component is added to the first component and comprises 0.3 g of β-TCP particles with an average diameter comprised in the range of 0.35 to 0.50 mm and a Ca/P molar ratio of 1.42. The second (liquid) component is a solution of 100 mg gentamycin sulphate in 1.6 ml of water.

The powder/liquid components were mixed together for 30 seconds and the resulting cement paste was filled into a syringe for application to a bone defect.

EXAMPLE 3

The first component (containing the powdered particles) consists of 1.3 g of β-TCP particles with an average diameter of 6 μm and a Ca/P molar ratio of 1.41 and 0.7 g of MCPM. The third component is added to the first component and comprises 0.8 g of hydroxyapatite (HA) particles with an average diameter comprised in the range of 0.35 to 0.50 mm. The second (liquid) component is a solution of 100 mg gentamycin sulphate in 1.6 ml of a 0.16 M aqueous sulphuric acid solution.

The powder/liquid components were mixed together for 30 seconds and the resulting cement paste was filled into a syringe for application to a bone defect.

EXAMPLE 4

1.5 g of β-TCP particles with an average diameter of 2 μm and a Ca/P molar ratio of 1.46, 0.3 g β-TCP particles with an average diameter comprised in the range of 0.35 to 0.50 mm and a Ca/P molar ratio of 1.42 and 1.5 ml of a solution of $H_3PO_4$ 3M, $H_2SO_4$ 0.1 M and $Na_2H_2P_2O_7$ 0.1 M were mixed together for 30 seconds, placed into a syringe and injected into a bony cavity.

EXAMPLE 5

1.5 g of β-TCP particles with an average diameter of 2 μm and a Ca/P molar ratio of 1.46, 0.3 g hydroxyapatite (HA) particles with an average diameter comprised in the range of 0.35 to 0.50 mm and 1.5 ml of a solution of $H_3PO_4$ 3M, $H_2SO_4$ 0.1 M and $Na_2H_2P_2O_7$ 0.1 M were mixed together for 30 seconds, placed into a syringe and injected into a bony cavity.

What is claimed is:

1. Cement for surgical purposes comprising:
   a first component comprising beta tertiary calciumphosphate (β-TCP) particles having a mean specific surface area of less than 10.000 $m^2/g$; and monocalcium phosphate (MCPA) particles or monocalcium phosphate monohydrate (MCPM) particles or phosphoric acid; and a setting rate controller; and
   a second component comprising water; and
   a third component comprising a calcium phosphate with a Ca/P ratio different from 1.5, said third component comprising particles having an average diameter which is larger than the average diameter of said β-TCP particles of said first component,
   whereby upon mixing of said three components a hardened mass comprising brushite (DCPD) is formed and said third component constitutes 1 to 99 volume-percent of said hardened mass.

2. Cement according to claim 1, characterized in that said first component comprises β-TCP particles and MCPA and MCPM particles.

3. Cement according to claim 1 or 2, characterized in that the setting time of said cement as measured at 25° C. is at least 2 minutes.

4. Cement according to claim 3, characterized in that the setting time of said cement as measured at 25° C. is at least 3 minutes.

5. Cement according to claim 4, characterized in that the setting time of said cement as measured at 25° C. is at least 5 minutes.

6. Cement according to claim 1, characterized in that the β-TCP particles have a mean specific surface area of 0.0137–2.000 $m^2/g$.

7. Cement according to claim 6, characterized in that the β-TCP particles have a mean specific surface area of 0.8–1.5 $m^2/g$.

8. Cement according to claim 7, characterized in that the setting rate controller is chosen from the group of sodium pyrophosphate, potassium pyrophosphate, sodium acetate, potassium acetate, sodium citrate, potassium citrate, sodium phosphocitrate, potassium phosphocitrate, sodium sulphate or potassium sulphate, calcium sulphate hemihydrate (CSH), sodium pyrophosphate (NaPPH), sodium dihydrogen pyrophosphate (NaHPP), calcium pyrophosphate (CaPP), magnesium sulphate and sodium or potassium biphosphonate.

9. Cement according to claim 1, characterized in that said second component further comprises orthophosphoric acid (OPA) and/or sulphuric acid (SA).

10. Cement according to claim 9, characterized in that the total weight $W_{TCP}$ of the β-TCP particles in the cement is larger than the weight $W_T = W_{MCPA}/0.7546 + W_{MCPM}/0.8127 + W_{OPA}0.3159 + W_{SA}/0.3162$ where $W_{MCPA}$, $W_{MCPM}$, $W_{OPA}$, and $W_{SA}$ are, respectively, the weights of MCPA, MCPM, OPA and SA used.

11. Cement according to claim 10, characterized in that the weight $W_{TCP}$ is in the range of $1.2\ W_T \leq W_{TCP} \leq 10.0\ W_T$.

12. Cement according to claim 11, characterized in that the weight $W_{TCP}$ is in the range of $2\ W_T \leq W_{TCP} \leq 5\ W_T$.

13. Cement according to claim 1, characterized in that the average particle diameter of said third component is at least two times larger than the average diameter of said β-TCP particles of said first component.

14. Cement according to claim 1, characterized in that the average particle diameter of said third component is in the range of 50 to 2000 μm.

15. Cement according to claim 1, characterized in that said third component comprises hydroxyapatite particles.

16. Cement according to claim 1, characterized in that said third component comprises polymeric particles.

17. Cement according to claim 1, characterized in that two different types of β-TCP particles are used,
   the first type being particles having a median particle size of 5 μm with less than 10 volume % of the particles being smaller than 1 μm; and
   the second type being particles having an average diameter in the range of 150 to 500 μm.

18. Cement according to claim 1, characterized in that the Ca/P atomic ratio of the μ-TCP particles of said first component is comprised between 1.350 to 1.499.

19. Cement according to claim 18, characterized in that said Ca/P atomic ratio is comprised between 1.455 to 1.465.

20. Cement according to claim 1, characterized in that one of the three components further comprises a biodegradable polymer.

21. Cement according to claim 20, characterized in that the biodegradable polymer is selected from the group of polysaccharide derivatives; chitin derivatives; xanthan gum; agarose; polyethyleneglycols (PEG), polyhydroxyethylenemethacrylates (HEMA); synthetic and natural proteins; or collagens.

22. Cement according to claim 9, characterized in that the volume $V_L$ of the second component is equal or larger than the volume $V_T$ ($W_{MCPA} \times 0.615 + W_{MCPM} \times 0.5 + W_{OPA} \times 1.102 + W_{SA} \times 1.101$) ml/g of the first component.

23. Cement according to claim 22, characterized in that the relation of volume $V_L$ of the second component and of $V_T$ of the first component is in the range of $0.5\ V_T \leq V_L \leq 10.0\ V_T$.

24. Cement according to claim 1, characterized in that said first component further comprises pharmaceutically or physiologically active substances.

25. Cement according to claim 24, characterized in that said antibiotics is selected from the group of: aminoglycosides, vancomycins, gentamycins or salts thereof.

26. Cement according to claim 24, characterized in that said antibiotics is a mixture of two different aminoglycosides.

27. Cement according to claim 1, characterized in that the first component comprises at least 50 weight percent of β-TCP.

28. Cement according to claim 1, characterized in that the particles of said third component are made from another material than β-TCP.

29. Cement according to claim 28, characterized in that the particles of said third component are made from a material selected from the group of: hydroxyapatite; biphasic calcium phosphonate (HA/β-TCP) mixtures; bioglasses; or polymeric materials.

30. Cement according to claim 1, characterized in that the third component is a calcium phosphate with a Ca/P ratio lower than 1.5.

31. Cement according to claim 1, characterized in that the third component is a calcium phosphate with a Ca/P ratio higher than 1.5.

32. Method for producing a matrix of brushite (DCPD) as temporary bone replacement material characterized in that said three components according to claim 1 are mixed together and allowed to harden.

33. Temporary bone replacement material obtained by the method according to claim 32, characterized in that it comprises brushite (DCPD).

34. Temporary bone replacement material according to claim 32, wherein said third component comprises β-TCP particles and said temporary bone replacement material is characterized in that it comprises β-TCP particles of said third component embedded in said brushite matrix.

* * * * *

UNITED STATES PATENT AND TRADEMARK OFFICE
CERTIFICATE OF CORRECTION

PATENT NO. : 6,425,949 B1
DATED : July 30, 2002
INVENTOR(S) : Lemaitre et al.

It is certified that error appears in the above-identified patent and that said Letters Patent is hereby corrected as shown below:

Column 2,
Line 13, delete "$Ca(H_{2PO4})_2, H_2O$" and insert -- $Ca(H_2PO_4)_2$ --

Column 3,
Line 20, delete "03159" and insert -- 0.3159 --.

Column 7,
Line 9, delete "µ-TCP" and insert -- ß-TCP --.

Signed and Sealed this

Tenth Day of December, 2002

JAMES E. ROGAN
*Director of the United States Patent and Trademark Office*